(12) United States Patent
Kirk et al.

(10) Patent No.: US 6,575,952 B2
(45) Date of Patent: Jun. 10, 2003

(54) ABSORBENT ARTICLE HAVING A MULTILAYER ABSORBENT CORE

(75) Inventors: Robert Rex Kirk, Hawthornedene (AU); Jody Dorothy Suprise, Pine River, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 50 days.

(21) Appl. No.: 09/854,361

(22) Filed: May 11, 2001

(65) Prior Publication Data

US 2002/0169430 A1 Nov. 14, 2002

(51) Int. Cl.$^7$ ................................................ A61F 13/15
(52) U.S. Cl. ........................................ 604/386; 604/378
(58) Field of Search ................................ 604/378, 365, 604/368, 369, 374, 385.21

(56) References Cited

U.S. PATENT DOCUMENTS

| | | |
|---|---|---|
| 4,610,678 A | 9/1986 | Weisman et al. |
| 4,673,402 A | 6/1987 | Weisman et al. |
| 5,188,624 A | 2/1993 | Young, Sr. et al. |
| 5,334,177 A | 8/1994 | Cohen |
| 5,364,382 A | 11/1994 | Latimer et al. |
| 5,429,629 A | 7/1995 | Latimer et al. |
| 5,486,166 A | 1/1996 | Bishop et al. |
| 5,486,167 A | 1/1996 | Dragoo et al. |
| 5,490,846 A | 2/1996 | Ellis et al. |
| 5,562,645 A * | 10/1996 | Tanzer et al. ............... 604/358 |
| 5,651,862 A | 7/1997 | Anderson et al. |
| 5,728,082 A | 3/1998 | Gustafsson et al. |
| 5,836,929 A | 11/1998 | Bewick-Sonntag et al. |
| 5,891,119 A | 4/1999 | Ta et al. |
| 5,916,670 A | 6/1999 | Tan et al. |
| 6,059,764 A | 5/2000 | Osborn, III et al. |
| 6,068,620 A | 5/2000 | Chmielewski |

FOREIGN PATENT DOCUMENTS

| | | |
|---|---|---|
| EP | 0 558 889 B1 | 9/1993 |
| EP | 0 719 531 A1 | 7/1996 |
| EP | 1 057 465 A1 | 12/2000 |
| FR | 2 656 794 | 7/1991 |
| WO | WO 98/47456 A1 | 10/1998 |
| WO | WO 99/63922 A1 | 12/1999 |
| WO | WO 99/63923 A1 | 12/1999 |
| WO | WO 99/63925 A1 | 12/1999 |
| WO | WO 00/29658 | 5/2000 |
| WO | WO 00/59439 A1 | 10/2000 |

OTHER PUBLICATIONS

U.S. patent application Ser. No. 09/854,360 filed May 11, 2001 by David A. Fell et al. for "Absorbent Article Having a Multilayer Blended Core and a Method of Forming".

Patent Cooperation Treaty Search Report from the International Search Authority, International Application No. PCT/US 02/06362 dated Oct. 2, 2002.

* cited by examiner

Primary Examiner—Weilun Lo
Assistant Examiner—Jamisue A Webb
(74) Attorney, Agent, or Firm—Thomas J. Connelly; Scott A. Baum

(57) ABSTRACT

An absorbent article, such as a thin incontinence pad or pantyliner, is disclosed which has a multilayered absorbent core for providing protection against involuntary urine loss. The absorbent article includes a liquid permeable bodyside liner, a liquid-impermeable baffle, and first and second absorbents positioned between the liner and the baffle. The first absorbent is a stabilized material containing a superabsorbent and has a predetermined basis weight. The second absorbent is positioned below the first absorbent and contains a different superabsorbent from the superabsorbent present in the first absorbent. The second absorbent has a basis weight that is equal or greater than the basis weight of the first absorbent.

25 Claims, 2 Drawing Sheets

ABSORBENT ARTICLE HAVING A MULTILAYER ABSORBENT CORE

FIELD OF THE INVENTION

This invention relates to an absorbent article having a multilayer absorbent core for containing body fluid expelled from a human body. More specifically, this invention relates to a thin incontinence pantyliner for absorbing and retaining urine.

BACKGROUND OF THE INVENTION

Absorbent articles such as catamenial pads, sanitary napkins, pantyliners, and the like, are designed to be worn adjacent to a woman's pudendum to absorb body fluid such as menses, blood, urine and other body excretions. It has been found that many women suffering from incontinence will buy and use a feminine care product, such as a pantyliner or a sanitary napkin, for the purpose of absorbing and retaining urine. Many incontinent men will also buy and/or wear feminine care products since they are readily, commercially available and these products may also be present in their household.

Incontinence users experience important differences from menstruating women and the use of commercially available feminine care products may not satisfy their specific needs. Most incontinence users require a product that can absorb and retain urine over an extended period of time. Since feminine care products are specifically designed to absorb and retain menses, many do not contain superabsorbents. Superabsorbents are capable of retaining large quantities of body fluid, such as urine, but it is known that they can impede the flow of menses. Without the presence of superabsorbents, many feminine care products do not have the fluid retention capacity needed by incontinence users. The presence of superabsorbents in incontinence products allows the liquid urine to be locked away so the product feels dry to the wearer. Many incontinence users tend to expel only a few drops of urine at a time and therefore they tend to wear their products over a longer time period. In addition, many incontinence users are older, frugal or on a fixed income and therefore some tend to wear their products for an extended period of time in order to save money. Another reason many incontinence users wear pantyliners or ultra thin catamenial pads for incontinence is that most incontinence products are thick and bulky rather than being thin and discreet. In our society, incontinence users have a strong psychological reason for not wanting other people to know that they suffer from incontinence.

Because of the above concerns, there is a need to produce a relatively inexpensive, thin incontinence pad or pantyliner, having a thickness of less than about 5 millimeters, which can absorb and retain from between about 20 grams to about 100 grams of urine.

Now, a relatively inexpensive, thin absorbent article has been invented that can do just that. This absorbent article contains an absorbent core formed from two or more layers of stabilized material, each containing a superabsorbent.

SUMMARY OF THE INVENTION

Briefly, this invention relates to an absorbent article, such as an incontinence pad or pantyliner, having an absorbent core formed from two or more layers of blended material to provide protection against involuntary loss of body fluids. The absorbent article includes a liquid permeable bodyside liner, a liquid-impermeable baffle, and first and second absorbents positioned between the liner and the baffle. The first absorbent is a stabilized material containing a superabsorbent and has a predetermined basis weight. The second absorbent is positioned below the first absorbent and contains a different superabsorbent from the superabsorbent present in the first absorbent. The second absorbent has a basis weight that is greater than the basis weight of the first absorbent.

The general object of this invention is to provide an absorbent article having an absorbent core formed from two or more layers for containing body fluid involuntarily expelled from a human body. A more specific object of this invention is to provide a thin incontinence pad or pantyliner for absorbing and retaining urine.

Another object of this invention is to provide an absorbent article that has a thickness of less than about 5 millimeters.

A further object of this invention is to provide a thin absorbent article that utilizes a two or more layer absorbent core, each containing a different superabsorbent.

Still another object of this invention is to provide a thin absorbent article that utilizes an absorbent core formed from two or more layers, each of which contains a different superabsorbent, and the second absorbent layer has a greater basis weight than the first absorbent.

Still further, an object of this invention is to provide a reasonably priced, thin absorbent article that is easy to manufacture.

Other objects and advantages of the present invention will become more apparent to those skilled in the art in view of the following description and the accompanying drawings.

DETAILED DESCRIPTION OF THE PREFERRED EMBODIMENTS

Figure 1:
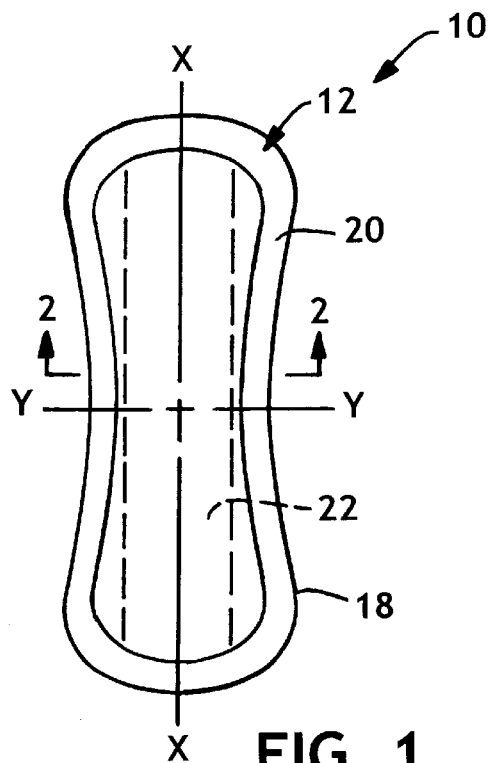
FIG. 1 is a top view of an absorbent article such as a thin incontinence pad or a pantyliner designed to absorb and retain urine.
Figure 2:
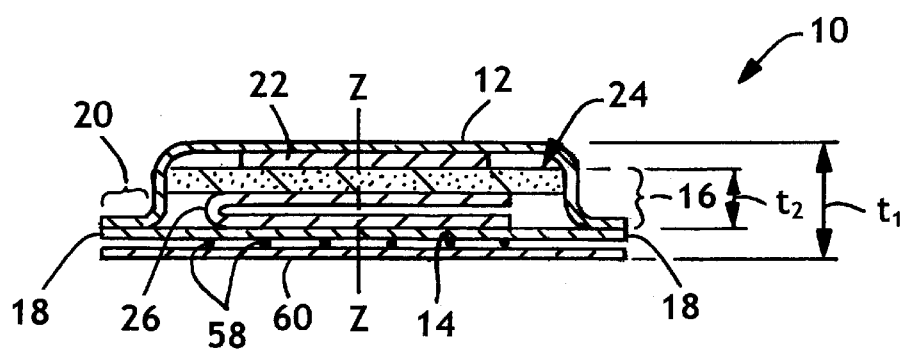
FIG. 2 is a cross-sectional view of the absorbent article shown in FIG. 1 taken along line 2—2 and showing first and second absorbent layers.

Referring to FIGS. 1 and 2, an absorbent article 10 is shown which is depicted as a thin incontinence pad or pantyliner. The absorbent article 10 is designed to be secured to an inside surface of a person's undergarment by a garment adhesive and is designed to absorb and retain urine that is involuntarily expelled from the body. The absorbent article 10 is an elongated product having a central longitudinal axis x—x, a central transverse axis y—y, and a vertical axis z—z. The absorbent article 10 is relatively thin. By "thin" it is meant that the absorbent article 10 has a thickness of less than about 5 millimeters. Preferably, the absorbent article 10 has a thickness of less than about 4 millimeters, and most preferably, the absorbent article 10 has a thickness of less than about 3.5 millimeters. The absorbent article 10 has a fluid retention capacity capable of absorbing from between about 20 grams to about 100 grams of urine. Preferably, the absorbent article 10 will be able to absorb about 50 grams of urine.

The absorbent article 10 includes a liquid permeable liner or cover 12, a liquid-impermeable baffle 14, and an absorbent core 16 positioned and enclosed between the liner 12 and the baffle 14. The bodyside liner 12 is designed to be in contact with the wearer's body. The bodyside liner 12 can be constructed of a woven or nonwoven material that is easily penetrated by body fluid, especially urine. The liner 12 can also be formed from either natural or synthetic fibers. Suitable materials include bonded-carded webs of polyester, polypropylene, polyethylene, nylon or other heat-bondable fibers. Other polyolefins, such as copolymers of polypropylene and polyethylene, linear low-density polyethylene, finely perforated film webs and net materials, also work well. A suitable material is a soft, wettable homopolymer spunbond having a basis weight of from between about 13 grams per square meter (gsm) to about 27 gsm. Another suitable material is an apertured thermoplastic film. Still another preferred material for the bodyside liner 12 is a spunbond web of polypropylene. The spunbond web can contain from between about one percent (1%) to about six percent (6%) of titanium dioxide pigment to give it a clean, white appearance. When the liner 12 is constructed from a spunbond web, it is desirable to use a uniform thickness of spunbond because it will provide sufficient strength to resist being torn or pulled apart during use. The most preferred polypropylene webs have a basis weight of from between about 13 to about 40 grams per square meter (gsm). An optimum basis weight is from between about 15 gsm to about 25 gsm. The thickness of the bodyside liner 12 can range from between 0.1 millimeters mm to about 1.0 mm.

It should be noted the bodyside liner 12 could be coated, sprayed or otherwise treated with a surfactant to make it hydrophilic. By "hydrophilic" it is meant that the bodyside liner 12 will have a strong affinity for water and a contact angle of less than 180 degrees. When the bodyside liner 12 is formed from a hydrophilic material, it will allow the body fluid to pass quickly therethrough. The bodyside liner 12 can also be embossed to improve the aesthetic appearance of the absorbent article 10.

The liquid permeable liner 12 and the liquid-impermeable baffle 14 cooperate to enclose and retain the absorbent core 16 therebetween. The liner 12 and the baffle 14 can be cut, sized and shaped to have a coterminous outer edge 18. When this is done the liner 12 and the baffle 14 can be bonded in face to face contact to form an absorbent article 10 having a peripheral seal or fringe 20. The peripheral fringe can be formed to have a width of about 5 millimeters. Preferably, the liner 12 and the baffle 14 will each have a generally dogbone or hourglass configuration. With a dog bone or hourglass configuration, the absorbent article 10 will have a narrow section located adjacent to the central transverse axis y—y that separates a pair of larger, end lobes. The end lobes can be sized and/or shaped differently, if desired. An absorbent article 10 having a dogbone or hourglass shape is more comfortable to wear than a generally rectangular shaped product. The absorbent article 10 can also be asymmetrical. The liner 12 and the baffle 14 can be bonded or sealed together about their periphery by a construction adhesive to form a unitary absorbent article 10. Alternatively, the liner 12 and the baffle 14 can be bonded together by heat, pressure, by a combination of heat and pressure, by ultrasonics, etc. to form a secure attachment.

The liquid-impermeable baffle 14 can be designed to permit the passage of air or vapor out of the absorbent article 10 while blocking the passage of body fluid, such as urine. The baffle 14 can be made from any material exhibiting these properties. The baffle 14 can also be constructed from a material that will block the passage of vapor as well as fluids, if desired. A good material for the baffle 14 is a micro-embossed, polymeric film, such as polyethylene or polypropylene. Bicomponent films can also be used. A preferred material is polyethylene film. Most preferably, the baffle 14 will be comprised of a polyethylene film having a thickness in the range of from between about 0.1 mm to about 1.0 mm.

Referring again to FIG. 2, the absorbent article 10 is shown having a transfer layer 22. The transfer layer 22 is optional and can be eliminated if desired. The transfer layer 22, which may contain a plurality of apertures formed therethrough, is positioned between the bodyside liner 12 and the absorbent core 16 and is aligned along the central longitudinal axis x—x. Preferably, the transfer layer 22 is positioned immediately below the bodyside liner 12 and is in direct face to face contact therewith. The transfer layer 22 can be adhesively bonded to the absorbent core 16, if desired, in order to facilitate a transfer of body fluid therebetween. The transfer layer 22 can extend over a portion of the length of the absorbent core 16 or it can extend over the entire length of the absorbent core 16. Preferably, the transfer layer 22, when present, will extend over at least 70% of the length of the absorbent core 16. Although the transfer layer 22 is optional, when present, it does provide good fluid movement of the urine downward from the bodyside liner 12 into the absorbent core 16. This downward movement of the urine is parallel to the vertical axis z—z. The z-axis is perpendicularly arranged relative to the x and y-axes. In addition, the transfer layer 22 inhibits the flow of urine from the absorbent core 16 back up into the liner 12. This phenomenon is commonly referred to as rewet. It is important that incontinence pads and pantyliners do not exhibit rewet because the consumer views it as an undesirable feature.

The transfer layer 22 can be constructed from a material that will provide good fluid transfer. Typical materials that can be used for the transfer layer 22 are spunbond, coform and carded webs. One useful material is a wettable nonwoven having a basis weight of from between about 13 gsm to about 50 gsm. The transfer layer 22 can be treated to make it hydrophilic. The thickness of the transfer layer 22 can range from between about 0.2 mm to about 1.0 mm. The transfer layer 22 can also be dyed to a different color than the color of the bodyside liner 12 and/or the absorbent core 16. A light blue, pink, or peach color has been found to be desirable, as these are pleasing colors to the ultimate consumer. The transfer layer 22 can alternatively be white in color yet will still be distinguishable from the bodyside liner 12 which may have a different shade of white. A benefit of making the transfer layer 22 a different color than the absorbent core 16 is that it presents a fluid target for the wearer.

It should be noted that the transfer layer 22 could be embossed to improve the aesthetic appearance of the absorbent article 10 since the transfer layer 22 is visible beneath the bodyside liner 12.

It is also possible to substitute a surge layer (not shown) for the transfer layer 22. The purpose of a surge layer is to quickly take up and temporarily hold the urine until the absorbent core 16 has adequate time to absorb the urine. The surge layer can be formed from various materials. Two good materials from which the surge layer can be formed include a crimped bicomponent spunbond or from a bonded carded web. When a surge layer is utilized, it should be designed to have a basis weight of from between about 30 gsm to about 85 gsm and a thickness ranging from between about 0.15 mm to about 2 mm. The following U.S. Patents teach surge layers: U.S. Pat. Nos. 5,364,382; 5,429,629; 5,490,846 and 5,486,166.

Still referring to FIG. 2, the absorbent article 10 has an absorbent core 16 that is positioned between the transfer layer 22 and the liquid-impermeable baffle 14. If no transfer layer is present, the absorbent core 16 is positioned between the bodyside liner 12 and the liquid-impermeable baffle 14. The absorbent core 16 includes a first absorbent 24 and a second absorbent 26. The first absorbent 24 is arranged close to the liner 12 and is positioned vertically above the second absorbent 26. The first absorbent 24 should be in direct face to face contact with the second absorbent 26. The first absorbent 24 can be adhered, for example, by an adhesive, to the second absorbent to ensure intimate contact and better fluid transfer therebetween. The first absorbent 24 is an airlaid material. Airlaid materials are commercially available from several manufacturers. Concert GmbH is one such supplier of airlaid material that can be used to construct the absorbent article 10. Concert GmbH has an office located at Am Lehmberg 10, 16928 Falkenhagen, Germany.

Even though it is preferred that the first and second absorbents, 24 and 26 respectively, be in direct contact with one another, it is possible to place one or more layers of tissue therebetween. Some manufacturers like to wrap an absorbent containing superabsorbent particles so as to prevent the superabsorbent particles from escaping from the finished product.

Figure 3:
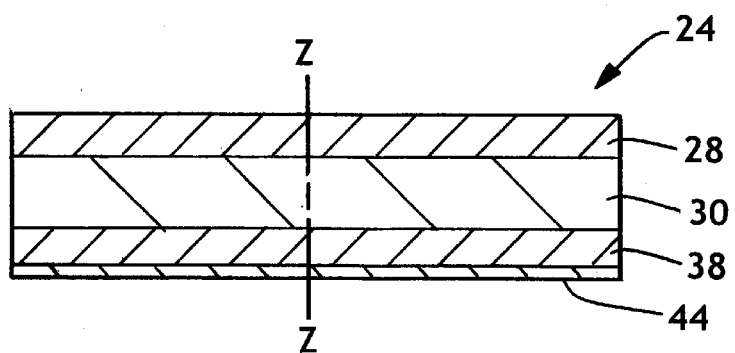
FIG. 3 is an enlarged cross-sectional view of the first absorbent shown in FIG. 2.
Figure 4:
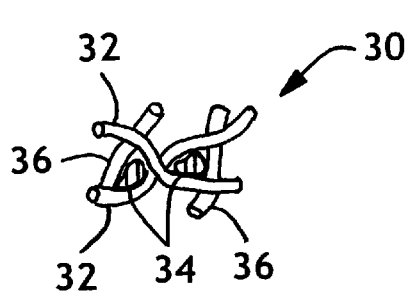
FIG. 4 is an enlarged view of a portion of the first absorbent shown in FIG. 3 depicting the composition of the second layer of the first absorbent.
Figure 5:
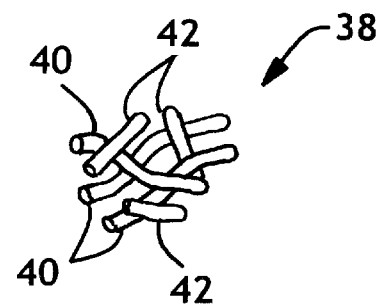
FIG. 5 is an enlarged view of a portion of the first absorbent shown in FIG. 3 depicting the composition of the third layer of the first absorbent.

Referring now to FIGS. 3–5, the first absorbent 24 is depicted as a multifunctional airlaid (MFAL) material having several distinct layers. The first absorbent 24 is shown having four layers in FIG. 3. The first absorbent 24 has a basis weight of less than about 250 gsm and can have a density of about 0.12 grams per cubic centimeter (g/cm$^3$). The four layers 28, 30, 38 and 44, arranged from top to bottom, form an integral first absorbent 24. The first layer 28 is a layer of polymer fibers. The polymer fibers 28 can be formed from polyethylene terephthalate and can be bonded together by a latex. The polymer fibers 28 represent from between about 10% to about 25% of the basis weight of the first absorbent 24. Preferably, the polymer fibers 28 represent from between about 15% to about 20% of the basis weight of the first absorbent 24. Most preferably, the polymer fibers 28 represent about 16% of the basis weight of the first absorbent 24.

Referring to FIGS. 3 and 4, the second layer 30 is immediately beneath the first layer 28 and includes cellulosic fibers 32, a superabsorbent 34 and a binder 36. The cellulosic fibers 30 can be pulp or fluff fibers. The cellulosic fibers 30 can also contain thermally bonded mercerized cellulose. The superabsorbent 34, present in the second layer 30, can be in the form of small particles, although fibers, flakes or other forms of superabsorbents can also be used. A superabsorbent is a material that is capable of absorbing at least 10 grams of water per gram of superabsorbent material. Preferably, the superabsorbent 34 is in the form of a plurality of small particles. The superabsorbent 34 should be capable of rapidly absorbing body fluid, especially urine, which passes downward from the polymer layer 28. Two suitable superabsorbents that can be used are FAVOR 1180 and FAVOR 3950. Both FAVOR 1180 and FAVOR 3950 are commercially available from Stockhausen, Inc. having an office located at 2408 Doyle Street Greensboro, N.C. 27406. Other similar types of superabsorbents can also be used. The superabsorbent 34 should have a basis weight of from between about 40 gsm to about 80 gsm. Preferably, the superabsorbent 34 has a basis weight of from between about 50 gsm to about 60 gsm. Most preferably, the superabsorbent 34 has a basis weight of about 56 gsm. The superabsorbent 34 can represent from between about 20% to about 30% of the basis weight of the first absorbent 24. Preferably, the superabsorbent 34 can represent from between about 20% to about 25% of the basis weight of the first absorbent 24. Most preferably, the superabsorbent 34 can represent about 23% of the basis weight of the first absorbent 24.

The binder 36 used in the second layer 30 can be a coating but preferably is in the form of binder fibers. The binder fibers 36 can be bicomponent fibers each having a polyethylene terephthalic core surrounded by a polyethylene sheath. Alternatively, the binder fibers 36 can be bicomponent fibers each having a polypropylene core surrounded by a polyethylene sheath.

The second layer 30 can represent from between about 40% to about 70% of the basis weight of the first absorbent 24. Preferably, this second layer 30 represents from between about 40% to about 50% of the basis weight of the first absorbent 24. Most preferably, the second layer 30 represents about 45% of the basis weight of the first absorbent 24.

Referring to FIGS. 3 and 5, the third layer 38 making up the first absorbent 24 is formed from cellulosic fibers 40 and a binder 42. This third layer 38 can be formed from multi-bonded compressible cellulose wherein the binder 42 is in the form of binder fibers. The binder fibers 42 can be bicomponent fibers each having a polyethylene terephthalic core surrounded by a polyethylene sheath. Alternatively, the binder fibers 36 can be bicomponent fibers each having a polypropylene core surrounded by a polyethylene sheath. The third layer 38 can represent from between about 25% to about 50% of the basis weight of the first absorbent 24. Preferably, the third layer 38 represents from between about 30% to about 40% of the basis weight of the first absorbent 24. Most preferably, the third layer 30 represents about 33% of the basis weight of the first absorbent 24.

The fourth or bottom layer 44 making up the first absorbent 24 is a layer of tissue. The layer of tissue 44 functions as a carrier sheet and can represent from about 1% to about 10% of the basis weight of the first absorbent 24. Preferably, the fourth layer 44 represents from between about 3% to about 8% of the basis weight of the first absorbent 24. Most preferably, the fourth layer 44 represents about 6% of the basis weight of the first absorbent 24.

Referring again to FIGS. 1 and 2, the first absorbent 24 is depicted as having a shaped periphery in the form of a dog-bone configuration. Other shapes, such as an hourglass shape, an oval shape a trapezoid shape, or an asymmetrical shape formed about the longitudinal axis, etc. can also be used. A peripheral shape, wherein the first absorbent 24 is narrowest in the middle along the central transverse axis y—y, works well for it will be more comfortable to wear. The first absorbent 24 is wider and has a larger surface area than the second absorbent 26. The first absorbent 24 functions to initially absorb and retain a majority of the urine that insults the absorbent article 10. As the first absorbent 24 becomes saturated, urine will move downward to the second absorbent 26 and will be retained therein. Preferably, the second absorbent 26 will absorb and retain a majority of the body fluid that insults the absorbent article 10.

Figure 6:
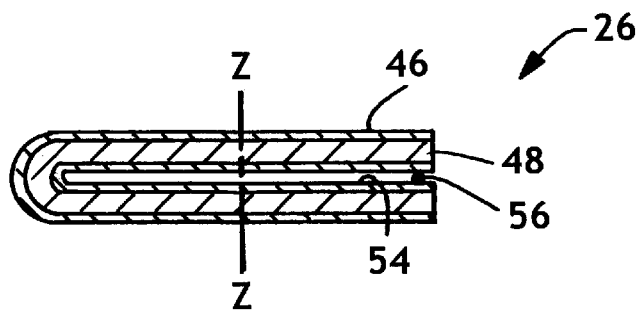
FIG. 6 is an enlarged cross-sectional view of the second absorbent depicting the U-shaped fold.
Figure 7:
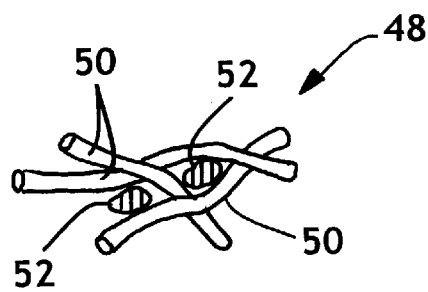
FIG. 7 is an enlarged view of a portion of the second absorbent shown in FIG. 6 depicting the composition of the cellulosic fiber/superabsorbent layer.

Referring now to FIGS. 2, 6 and 7, the second absorbent 26 of the absorbent core 16 is arranged nearer to the baffle 14 and is positioned vertically below the first absorbent 24. The second absorbent 26 is depicted as having a generally rectangular configuration and is slightly narrower in width than the first absorbent 24. By forming the second absorbent 26 into a generally rectangular shape, one can minimize waste during the manufacturing process and produce a lower cost absorbent article 10. The second absorbent 26 can have a length that equals the length of the first absorbent 24 but preferably is sized to be slightly shorter than the length of the first absorbent 24. Most preferably, the second absorbent 26 will have a length that ranges from between about 60% to about 95% of the length of the first absorbent 24. By sizing the second absorbent 26 to be slightly narrower in width and shorter in length than the first absorbent 24, the second absorbent 26 will have a smaller surface area than the first absorbent 24.

The second absorbent 26 is formed from a first layer of tissue 46, a layer 48 comprised of cellulosic fibers 50 and a superabsorbent 52, and a second layer of tissue 54. The first and second layers of tissue 46 and 54 function as carrier sheets for the layer 48. The second absorbent 26 is commercially available from Se Gyeong Company Ltd. which has an office located at 544 Silli-li, Bugan-myeon, Yeong chung-city, Kyeong buk, Korea.

The superabsorbent 52 present in the second absorbent 26 is preferably in the shape of small particles, although fibers, flakes or other forms of superabsorbents can also be used. A superabsorbent is a material that is capable of absorbing at least 10 grams of water per gram of superabsorbent material. The superabsorbent 52 utilized in the second absorbent 26 should be a different type and possess different characteristics from the superabsorbent 34 used in the first absorbent 24. By using different types of superabsorbents 34 and 52 in the first and second absorbents, 24 and 26 respectively, one can easily modify the absorbent article 10 to meet the specific needs of the consumer. The superabsorbent 52 should represent from between about 20% to about 30% of the basis weight of the second absorbent 26.

The second absorbent 26 should have a basis weight that is greater than the basis weight of the first absorbent 24. Preferably, the basis weight of the second absorbent 26 should be at least 30 gsm, and preferably, 40 gsm greater than the basis weight of the first absorbent 24. Furthermore, the basis weight of the second absorbent 26 should be more than about 250 gsm. Preferably, the basis weight of the second absorbent 26 should be more than about 275 gsm.

Referring to FIG. 6, the first layer of tissue 46 can represent from between about 5% to about 25% of the basis weight of the second absorbent 26. The layer 48 made up of the cellulosic fibers 50 and the superabsorbent particles 52 can represent from between about 50% to about 90% of the basis weight of the second absorbent 26. And the second layer of tissue 54 can represent from between about 5% to about 25% of the basis weight of the second absorbent 26.

Still referring to FIG. 6, one means of increasing the basis weight of the second absorbent 26 is by folding or doubling it upon itself. In FIG. 6, the second absorbent 26 is longitudinally folded into a U-shaped configuration. A line of adhesive 56 is positioned between the open ends of the U-shaped configuration so as to maintain the profile of the second absorbent 26. The line of adhesive 56 can be continuous or intermittent. The folding of the second absorbent 26 doubles its basis weight. By controlling the basis weight of the second absorbent 26, one can be assured that the second absorbent 26 will be able to retain a greater quantity of body fluid than the first absorbent 24. By retaining a majority of the body fluid in the second or lower absorbent 26, which is located away from the body of the wearer, the first absorbent 24 will be drier. This feature creates a more comfortable absorbent article 10 that will feel drier to the user.

Referring back to FIG. 2, the absorbent article 10 is shown having a thickness $t_1$ of less than about 5 mm. Preferably, the absorbent article 10 has a thickness $t_1$ of from between about 3 mm to about 5 mm. More preferably, the absorbent article 10 has a thickness $t_1$ of about 3.5 mm. The thickness $t_1$ or caliper of the absorbent article 10 can be determined by measuring the thickness $t_1$ of the absorbent article 10 with a bulk tester such as a Digimatic Indicator Gauge, type DF 1050E which is commercially available from Mitutoyo Corporation of Japan. Typical bulk testers utilize a smooth platen that is connected to the indicator gauge. The platen has dimensions that are smaller than the length and width of the second absorbent 26. The thickness of the absorbent article 10 is measured under a pressure of 0.35 kPa.

Still referring to FIG. 2, the absorbent core 16 also has a thickness $t_2$ of less than about 4 mm. Preferably, the absorbent core 16 has a thickness $t_2$ ranging from between about 2 mm to about 4 mm. More preferably, the absorbent core 16 has a thickness $t_2$ of less than about 3 mm. The thickness $t_2$ of the absorbent core 16 can be measured in a similar fashion as the thickness $t_1$ of the absorbent article 10 except that the absorbent core 16 will first be removed from the absorbent article 10.

The absorbent article 10 further is shown having a garment adhesive 58 secured to an exterior surface of the baffle 14. The garment adhesive 58 can be a hot or cold melt adhesive that functions to attach the absorbent article 10 to the inner crotch portion of an undergarment during use. The garment adhesive 58 enables the absorbent article 10 to be properly aligned and retained relative to the user's urethra so that maximum protection from the involuntary loss of urine can be obtained. The garment adhesive 58 can be slot coated onto the baffle 14 as one or more strips or it can be applied as a swirl pattern. The composition of the garment adhesive 58 is such that it will allow a user to remove the absorbent article 10 and reposition the article 10 in the undergarment if needed. A suitable garment adhesive 58 that can be used is Code Number 34-5602 which is commercially available from National Starch and Chemical Company. National Starch and Chemical Company has an office located at 10 Finderne Avenue, Bridgewater, N.J. 08807.

In order to protect the garment adhesive 58 from contamination prior to use, a releasable peel strip 60 is utilized. The peel strip 60 can be formed from paper or treated paper. A standard type of peel strip 60 is a white Kraft peel paper coated on one side so that it can be easily released from the garment adhesive 58. The user removes the peel strip 60 just prior to attaching the absorbent article 10 to the inner crotch portion of his or her undergarment. Three suppliers of the peel strips 60 include Tekkote, International Paper Release Products, and Namkyung Chemical Ind. Co., Ltd. Tekkote has an office located at 580 Willow Tree Road, Leonia, N.J. 07605. International Paper Release Products has an office located at 206 Garfield Avenue, Menasha, Wis. 54952. Namkyung Chemical Ind. Co., Ltd. has an office located at 202-68 Songsan-ri, Taean-eup, Hwaseoung-kum, Kyunggi, Korea.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. An absorbent core for an absorbent article, said absorbent core comprising a first absorbent formed of a layer of polymer fibers, a layer of cellulosic fibers, a superabsorbent and a binder; a first layer of cellulosic fibers; and a layer of tissue, said first absorbent having a basis weight of less than 250 gsm, and a second absorbent formed of a first layer of tissue, a layer of cellulosic fiber and a superabsorbent, and a second layer of tissue, and said second absorbent having a basis weight of more than 250 gsm.

2. An absorbent core for an absorbent article, said absorbent core comprising a first absorbent formed of an airlaid material and having a layer of polymer fibers, a layer of cellulosic fibers, a superabsorbent and a binder; a first layer of cellulosic fibers; and a layer of tissue, said first absorbent having a basis weight of less than 250 gsm, and a second absorbent formed of a first layer of tissue, a layer of cellulosic fiber and a superabsorbent; and a second layer of tissue, and said second absorbent having a basis weight of more than 275 gsm.

3. An absorbent article, comprising:
a) a liquid permeable liner;
b) a liquid-impermeable baffle;
c) a first absorbent positioned between said liner and said baffle, said first absorbent being a stabilized material containing a superabsorbent, and having a predetermined basis weight; and
d) a second absorbent positioned between said first absorbent and said baffle, said second absorbent folded into a U-shape and containing a different superabsorbent from said superabsorbent present in said first absorbent, and said second absorbent having a basis weight which is greater than said basis weight of said first absorbent.

4. The absorbent article of claim 3 wherein said stabilized material is formed of a layer of polymer fibers, a layer of cellulosic fibers, a superabsorbent and a binder; a first layer of cellulosic fibers; and a layer of tissue, and said first absorbent has a basis weight of less than 250 gsm.

5. The absorbent article of claim 4 wherein said polymer fibers are formed from polyethylene terephthalate and are bonded together by a latex.

6. The absorbent article of claim 3 wherein said second absorbent is formed of a first layer of tissue, a layer of cellulosic fiber and a superabsorbent, and a second layer of tissue, and said second absorbent has a basis weight of more than 250 gsm.

7. The absorbent article of claim 6 wherein said second absorbent has a generally rectangular configuration.

8. The absorbent article of claim 3 wherein said U-shape has an open end and a line of adhesive is positioned adjacent to said open end to maintain said U-shaped profile.

9. An absorbent article, comprising:
a) a liquid permeable liner;
b) a liquid-impermeable baffle;
c) a first absorbent positioned between said liner and said baffle, said first absorbent being an airlaid material comprising a superabsorbent and polymer fibers formed from polyethylene terephthalate bonded together by a latex, said first absorbent having a pre-determined basis weight; and
d) a second absorbent positioned between said first absorbent and said baffle, said second absorbent containing a different superabsorbent than said superabsorbent present in said first absorbent, said second absorbent having a basis weight which is greater than said basis weight of said first absorbent, and said second absorbent having a smaller surface area than said first absorbent.

10. The absorbent article of claim 9 wherein said first and second absorbents each have a width and the width of said second absorbent is less than the width of said first absorbent.

11. The absorbent article of claim 10 wherein said first absorbent has a generally dogbone configuration.

12. The absorbent article of claim 10 wherein said first absorbent has a generally hourglass configuration.

13. The absorbent article of claim 9 having a fluid retention capacity of from between about 20 grams to about 100 grams.

14. The absorbent article of claim 13 having a fluid retention capacity of about 50 grams.

15. An absorbent article comprising:
a) a liquid permeable liner;
b) a liquid-impermeable baffle;
c) a first absorbent positioned between said liner and said baffle, said first absorbent being an airlaid material formed of a layer of polymer fibers, a layer of cellulosic fibers, a superabsorbent and a binder; a first layer of cellulosic fibers; and a layer of tissue, and said first absorbent has a basis weight of less than 250 gsm; and
d) a second absorbent positioned between said first absorbent and said baffle, said second absorbent formed of a first layer of tissue, a layer of cellulosic fiber and a superabsorbent, and a second layer of tissue, and said second absorbent has a basis weight of more than 250 gsm.

16. The absorbent article of claim 15 wherein said superabsorbent present in said first absorbent is in particle form.

17. The absorbent article of claim 15 wherein said second absorbent has a basis weight which is at least 30 gsm greater than said basis weight of said first absorbent.

18. The absorbent article of claim 17 wherein said second absorbent has a basis weight which is at least 40 gsm greater than said basis weight of said first absorbent.

19. The absorbent article of claim 17 wherein said absorbent article has a thickness of from between about 3 millimeters to about 5 millimeters.

20. An absorbent article comprising:
a) a liquid permeable liner;
b) a liquid-impermeable baffle;
c) a transfer layer positioned adjacent to said liner which is capable of directing body fluid downward away from said liner;
d) a first absorbent positioned adjacent to said transfer layer, said first absorbent being an airlaid material formed of a layer of polymer fibers, a layer of cellulosic fibers, a superabsorbent and a binder; a first layer of cellulosic fibers; and a layer of tissue, and said first absorbent has a basis weight of less than 250 gsm; and
e) a second absorbent positioned between said first absorbent and said baffle, said second absorbent formed of a first layer of tissue, a layer of cellulosic fiber and a superabsorbent, and a second layer of tissue, and said second absorbent has a basis weight of more than 275 gsm.

21. The absorbent article of claim 20 wherein said absorbent article has a thickness of less than about 5 millimeters.

22. The absorbent article of claim 20 wherein said layer of polymer fibers represents from between about 10% to about 25% of the basis weight of said first absorbent, said layer of cellulosic fibers, superabsorbent and binder represents from between about 40% to about 70% of the basis weight of said first absorbent, said first layer of cellulosic fibers represents from between about 25% to about 50% of the basis weight of said first absorbent, and said layer of tissue represents from between about 1% to about 10% of said first absorbent.

23. The absorbent article of claim 22 wherein said superabsorbent represent from between about 20% to about 30% of the basis weight of said first absorbent.

24. The absorbent article of claim 20 wherein said first layer of tissue represents from between about 5% to about 25% of the basis weight of said second absorbent, said layer of cellulosic fiber and superabsorbent represents from between about 50% to about 90% of the basis weight of said second absorbent and a superabsorbent, and a second layer of tissue represents from between about 5% to about 25% of the basis weight of said second absorbent.

25. The absorbent article of claim 24 wherein said superabsorbent represent from between about 20% to about 30% of the basis weight of said second absorbent.

* * * * *